(12) United States Patent
Tavildar et al.

(10) Patent No.: US 12,303,304 B2
(45) Date of Patent: May 20, 2025

(54) ELECTRODE DISCONNECT DETECTION

(71) Applicant: NuVasive, Inc., San Diego, CA (US)

(72) Inventors: Siddhi Tavildar, San Diego, CA (US);
Sean O'Connor, San Diego, CA (US);
Dmitry Novikov, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 18/336,742

(22) Filed: Jun. 16, 2023

(65) Prior Publication Data

US 2023/0414182 A1  Dec. 28, 2023

Related U.S. Application Data

(63) Continuation of application No. 17/488,673, filed on Sep. 29, 2021.

(51) Int. Cl.
*A61B 5/00* (2006.01)
*A61B 5/257* (2021.01)
*A61B 5/296* (2021.01)
*A61B 5/395* (2021.01)
*G08B 5/22* (2006.01)
*G08B 21/18* (2006.01)

(52) U.S. Cl.
CPC ............. *A61B 5/746* (2013.01); *A61B 5/257* (2021.01); *A61B 5/296* (2021.01); *A61B 5/395* (2021.01); *A61B 5/7221* (2013.01); *G08B 5/22* (2013.01); *G08B 21/18* (2013.01)

(58) Field of Classification Search
CPC ......... A61B 5/746; A61B 5/257; A61B 5/296; A61B 5/395; A61B 5/7221; G08B 5/22; G08B 21/18
See application file for complete search history.

(56) References Cited

U.S. PATENT DOCUMENTS

| 5,501,230 A | * | 3/1996 | Laribiere ............... A61B 5/276 |
| | | | 607/63 |
| 8,206,312 B2 | | 6/2012 | Farquhar |
| 9,066,701 B1 | | 6/2015 | Finley |
| 9,392,953 B1 | | 7/2016 | Gharib |
| 2005/0027177 A1 | | 2/2005 | Shin |
| 2009/0179777 A1 | | 7/2009 | Ishikawa |
| 2009/0221887 A1 | | 9/2009 | Mannheimer |
| 2010/0022935 A1 | | 1/2010 | Muller |
| 2010/0175483 A1 | | 7/2010 | O'Mahony |
| 2011/0184297 A1 | | 7/2011 | Vitali |
| 2012/0095360 A1 | | 4/2012 | Runney |
| 2013/0190638 A1 | | 7/2013 | Chon |
| 2013/0289426 A1 | | 10/2013 | Lakshminarayan |

(Continued)

FOREIGN PATENT DOCUMENTS

CN 108601549 * 2/2017 ........... A61B 5/7203

*Primary Examiner* — Hongmin Fan

(57) ABSTRACT

Disclosed examples include those directed to detecting and remediating detachment of electrodes from a patient. In an example, a system calculates a Pearson correlation coefficient between: (1) power spectral density of the noise and (2) power spectral density of a recorded signal (e.g., from an electrode being operated in free-run EMG mode). If the recorded signal correlates with the noise, then the system notifies the user of presence of noise (e.g., the fallen electrode). Otherwise, the recorded signal is considered as the signal of interest (e.g., a valid EMG signal).

20 Claims, 9 Drawing Sheets

(56) References Cited

U.S. PATENT DOCUMENTS

| | | |
|---|---|---|
| 2015/0204745 A1 | 7/2015 | Marrota |
| 2015/0208939 A1 | 7/2015 | Zigel |
| 2016/0081560 A1 | 3/2016 | Hayter |
| 2018/0165923 A1* | 6/2018 | Schmit ................ A61B 5/6843 |
| 2020/0130433 A1 | 4/2020 | Stewart |
| 2023/0116830 A1 | 4/2023 | Tavildar |

* cited by examiner

ELECTRODE DISCONNECT DETECTION

CROSS REFERENCE TO RELATED APPLICATIONS

This application claims priority to and is a Continuation of U.S. patent application Ser. No. 17/488,673, filed Sep. 29, 2021, which application is incorporated herein by reference in its entirety herein.

BACKGROUND

Neuromonitoring can be used during a surgical procedure to reduce the risk of nerve damage. Neuromonitoring techniques can include causing electrical stimulation via electrodes located on surgical accessories and monitoring electromyography (EMG), motor evoked potential (MEP), or somatosensory evoked potential (SSEP) responses of nerves using recording electrodes placed on the patient. Other neuromonitoring techniques include free-run EMG, during which a neuromonitoring system listens for signals characteristic of muscle contractions.

Electrodes used for neuromonitoring are typically adhered to the surface of the patient's skin. But these electrodes can be accidentally removed or fall off, which can result in the electrodes providing incorrect signals until the detached electrode is observed by a user. Inadvertent disconnection of an electrode during neuromonitoring can result in different than expected results. For example, a disconnected electrode may be unable to detect a signal characteristic of activation of a nerve, but this inability may not be readily discernable because detecting such a signal may be relatively rare. As a result, the surgical team or a neuromonitoring device may fail to detect nerve responses getting weaker. Typically, nerve responses are monitored overtime, so if the surgery is damaging the nerve, the nerve's response may gradually weaken or even disappear. But if a connection with a nerve (or a muscle it innervates) is lost without noticing, a user or device may incorrectly conclude that the nerve is healthy. The reverse might also be true: if the user or device mistakenly believes that the detached electrode is still attached, they might think the nerve is not responding to stimulation. They might then take steps to save the nerve that would not be necessary (e.g. ending the surgery early or modifying retraction). Since there are often many recording sites, the identification of incorrect signals in a timely manner can be difficult during surgery. In addition, an individual performing the neuromonitoring may be some distance away from the patient (e.g., in a distant region of the operating room, another room in the surgical center, or entirely remote), which may affect their ability to readily see whether particular electrodes are connected or disconnected. There are further disadvantages in failing to detect detached electrodes, such as wasted computing resources spent processing irrelevant data corresponding to the detached electrodes. Rapid detection and remediation of a disconnected electrode can permit the use of neuromonitoring during surgery to aid in the diagnosis, correction, and treatment of nerve issues.

SUMMARY

In an example, there is a method comprising, during a surgical procedure, obtaining an electrode signal from a channel, determining that the electrode signal is characteristic of an electrode disconnected from a patient, and responsive to the electrode signal being characteristic of an electrode disconnected from a patient, performing remediation.

Determining whether the electrode signal is characteristic of an electrode disconnected from a patient can include comparing the electrode signal with a noise signal. The method can further include processing the electrode signal to form a processed electrode signal. The step of determining whether the electrode signal is characteristic of an electrode disconnected from a patient can include comparing the processed electrode signal with a stored processed noise signal.

The method can include, prior to the comparing, obtaining a noise signal, processing the noise signal, and storing the processed noise signal as the processed noise signal. The determining whether the electrode signal is characteristic of an electrode disconnected from a patient can include comparing a power spectral density of the electrode signal with a power spectral density of a noise signal. The comparing can include determining an amount of linear correlation between the power spectral density of the electrode signal with the power spectral density of the noise signal. The comparing can include calculating a Pearson correlation coefficient based on the power spectral density of the electrode signal with the power spectral density of the noise signal. The method can further include preventing performance of a neuromonitoring process on the electrode signal. The method can further include: adhering a plurality of electrodes to a patient; during the surgical procedure and after adhering the plurality of electrodes, obtaining a prior electrode signal from the channel; determining that the prior electrode signal is not characteristic of an electrode disconnected from a patient; and performing neuromonitoring with the prior electrode signal. A first electrode of the plurality of electrodes is electrically coupled to the channel and becomes disconnected subsequent to obtaining the prior electrode signal and before obtaining the electrode signal. Performing the remediation can include providing an alert indicating that the electrode is disconnected from the patient.

In a further example, the system includes one or more electrodes and one or more processors. The one or more processors are configured to perform electromyography with the one or more electrodes, and detect and remediate disconnection of a selected electrode of the one or more electrodes from a patient based on a comparison with noise. In an example, to detect the disconnection includes calculating a Pearson correlation coefficient between power spectral density of known noise and a power spectral density of an electrode signal corresponding to the selected electrode. In an example, to detect the disconnection includes determining whether the Pearson correlation coefficient indicates sufficient correlation between the power spectral density of known noise and the power spectral density of the electrode signal. The electromyography can include free-run electromyography. In an example, to remediate the disconnection includes to provide an alert to a user indicating that the selected electrode is disconnected. The system can further include a patient module electrically connected between the one or more electrodes and a controller. The patient module includes at least one of the one or more processors.

In another example, there is a system that includes one or more electrodes coupled to one or more channels. The system implements a neuromonitoring pipeline configured to: obtain an electrode signal from a selected channel of the one or more channels, apply disconnect detection to the electrode signal, and use the electrode signal in neuromonitoring. To apply the disconnect detection can include to calculate a correlation coefficient between power spectral density of known noise and power spectral density of the electrode signal, and determine whether the correlation coefficient satisfies a threshold. The neuromonitoring pipeline can be configured to apply noise reduction to the electrode signal prior to applying disconnect detection to the electrode signal and prior to using the electrode signal in neuromonitoring. To apply disconnect detection to the electrode signal can include to process the electrode signal with machine learning framework trained to recognize noise.

DETAILED DESCRIPTION

Disclosed examples include techniques for detecting and remediating disconnection of electrodes from a patient. A technique can include calculating the Pearson correlation coefficient between: (1) the power spectral density of known line noise and (2) the power spectral density of a recorded signal (e.g., a free-run EMG signal). If the recorded signal correlates with the noise, then the system can implement a remediation, such as notifying the user to reattach the electrode or disregarding signals from that electrode. Otherwise, the recorded signal is considered as a signal of interest (e.g., a valid EMG signal). The technique can be used to detect the environmental noise (e.g., line noise) in many different geographies regardless of region-specific line noise frequency (e.g., 60 Hz in the United States or 50 Hz in parts of Europe). The computational cost of the technique is sufficiently low that it can be implemented using hardware, software, or combinations thereof to execute in near real time (e.g., with a delay sufficiently small as to have no meaningful effect on the use of the system by the user to conduct neuromonitoring). Detection and remediation techniques described herein can be implemented to improve prior neuromonitoring systems by increasing reliability through rapid detection and correction of an error state (e.g., receiving a signal not representative of desired data) in which an incorrect signal was being monitored. Whereas previously users would remedy the issue by noticing a detached electrode, disclosed techniques can include those not reasonably performable by a person (e.g., signal processing techniques). An example system that benefits from use of the techniques described herein is shown in FIG. 1.

Figure 1:
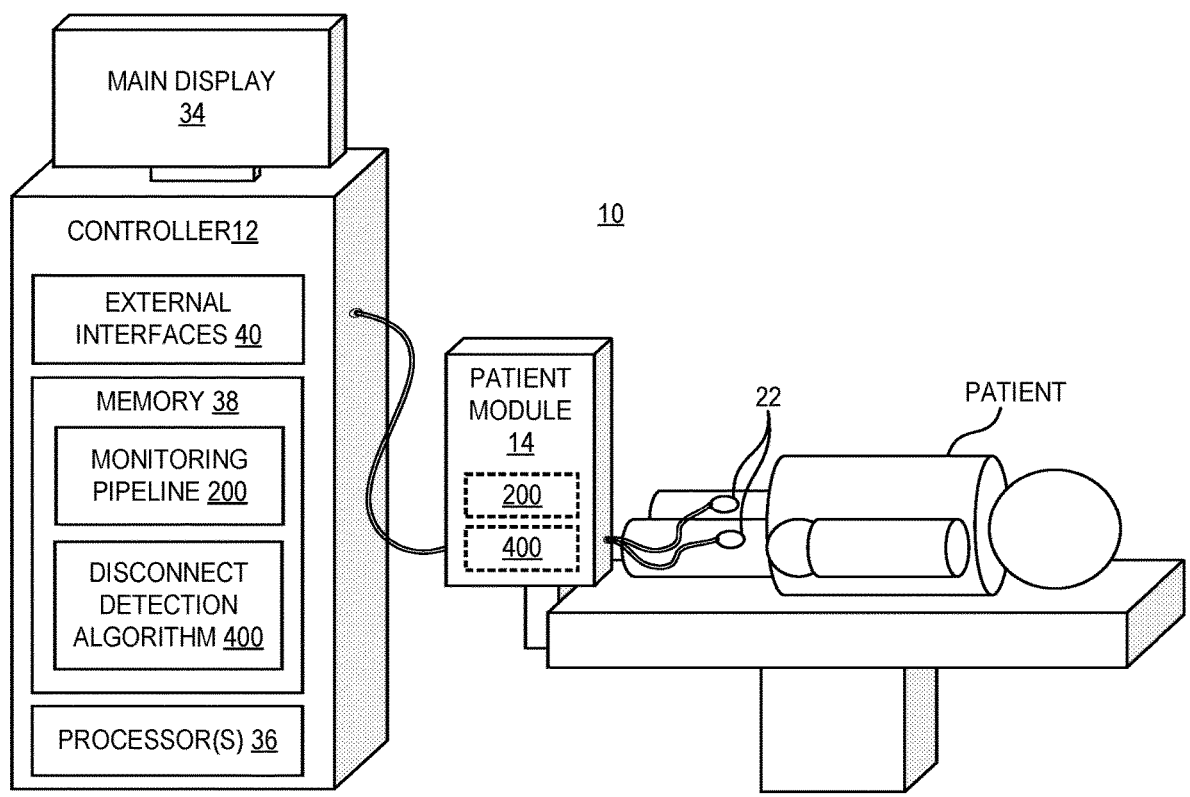
FIG. 1 illustrates example components of a neurophysiology system that can benefit from techniques described herein.

FIG. 1 illustrates example components of a neurophysiology system 10 that benefits from techniques described herein. The illustrated example neurophysiology system 10 includes a controller 12, a patient module 14, and a display 34, and one or more electrodes 22. In the illustrated example, the controller 12 and the patient module 14 cooperate to provide neuromonitoring as part of the system 10.

The controller 12 can be a surgical technology platform for use in an operating room. The controller 12 can provide one or more surgical applications (e.g., navigation, surgical planning, imaging, rod bending, robot control, other applications, or combinations thereof) and can control one or more aspects of the system 10. An example implementation of the controller 12 is a portable unit movable within or between operating rooms and usable during an operation to interact with one or more of multiple surgical applications. The controller 12 can include one or more processors 36 and memory 38.

The one or more processors 36 are one or more physical or virtual components configured to execute instructions. The instructions can be obtained from another component (e.g., from the memory 38), be stored in a respective processor 36 itself, be encoded in the configuration of the respective processor 36 (e.g., the instructions can be the arrangement of hardware gates or logic blocks of the respective processor 36), other ways, or combinations thereof. In many examples, the one or more processors 36 are central processing units, but can take other forms such as microcontrollers, microprocessors, graphics processing units, tensor processing units, other processors, or combinations thereof. In an example, the one or more processors 36 include both a central processing unit (e.g., those provided by INTEL or AMD) and a workstation-grade graphics card (e.g., those provided by NVIDIA or AMD).

The memory 38 is one or more physical or virtual components configured to store information, such as data or instructions. In some examples, the memory 38 includes the computing environment's main memory (e.g., random access memory) or long-term storage memory (e.g., a solid state drive). The memory 38 can be transitory or non-transitory computer-readable or processor-readable storage media. As illustrated, the memory 38 can store information sufficient to implement a monitoring pipeline 200, a disconnect detection algorithm 400, or other aspects described herein. The specifics of such aspects are described later herein, but generally such aspects can be implemented as or using program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages (e.g., C, C++, C#, Java, and Python) using various libraries provided with or for such languages (e.g., standard libraries).

The external interfaces 40 are a set of one or more components by which the controller 12 can provide output or receive input (e.g., from components external to the controller 12). For example, the external interfaces 40 can include one or more user input components, such as one or more sensors, buttons, pointers, keyboards, mice, gesture controls, touch controls (e.g., touch-sensitive strips or touch screens), eye trackers, voice recognition controls (e.g., microphones coupled to appropriate natural language processing components), other user input components, or combinations thereof. The external interfaces 40 can include one or more user output components, such as one or more lights, displays, speakers, haptic feedback components, other user output components, or combinations thereof. The external interfaces 30 can further include one or more components configured to provide output to or receive input from other devices, such as one or more ports (e.g., USB ports, THUNDERBOLT ports, serial ports, parallel ports, Ethernet ports) or wireless communication components (e.g., components configured to communicate according to one or more radiofrequency protocols, such as WI-FI, BLUETOOTH, ZIG-BEE, or other protocols). In some examples, the external interface 40 includes video input ports to obtain video or image input from devices, such as a C-arm or exoscope. In an example, the external interfaces 40 include: a touch display interface, local client interfaces, camera interface, imaging interfaces, video input, video output, USB interfaces, and remote monitoring interfaces. A USB interface can provide capabilities for USB file system access for exporting log files, screenshots, reports, and diagnostics, as well as importing DICOM or other data.

The patient module 14 is communicatively linked to the controller 12. The patient module 14 can be a device configured to facilitate the connection of neuromonitoring features (e.g., the one or more electrodes 22) and the controller 12. For instance, the patient module 14 can include ports for coupling the one or more electrodes 22 and provide relatively low-level functionality for the electrodes. The patient module 14 can then provide information regarding the electrodes (e.g., signals received therefrom) to the controller for analysis and use. Other components can include signal conditioning circuitry, stimulator drive circuitry, steering circuitry, and signal conditioning circuitry required to perform functional modes of the neurophysiology system 10, including but not necessarily limited to static pedicle integrity testing ("Basic Stimulated EMG"), dynamic pedicle integrity testing ("Dynamic Stimulated EMG"), nerve proximity detection ("XLIF"), neuromuscular pathway assessment ("Twitch Test"), motor evoked potential monitoring ("MEP Manual" and "MEP Automatic"), somatosensory evoked potential monitoring ("SSEP Manual" and "SSEP Automatic"), non-evoked monitoring ("Free-run EMG"), and surgical navigation ("Navigated Guidance"). In one example, the patient module 14 includes thirty-two recording channels and eleven stimulation channels. A display (e.g. an LCD screen) may be provided on the face of the patient module 14, and may be utilized for showing simple status readouts (for example, results of a power on test, the electrode harnesses attached, and impedance data, etc.) or more procedure related data (for example, a stimulation threshold result, current stimulation level, selected function, etc.). The patient module 14 may be positioned near the patient in the sterile field during surgery. By way of example, the patient module 14 may be attached to bed rail with the aid of a hook attached to, or forming a part of, the patient module 14 casing.

The patient module 14 can cooperate with the controller 12. The controller 12 can include computer hardware necessary to execute software that commands the stimulation source (e.g. via the patient module 14), receives digital and/or analog signals and other information from the patient module 14, processes EMG, MEP, and SSEP response signals, and displays the processed data to the operator via the display 34. Functions of the software within the controller 12 can include receiving user commands via the display 34 (e.g., via a touchscreen capability thereof), activating stimulation in the appropriate mode (e.g., Basic Stimulated EMG, Dynamic Stimulated EMG, XLIF, MEP automatic, MEP manual, SSEP automatic, SSEP manual, and Twitch Test), processing signal data according to defined algorithms, displaying received parameters and processed data, and monitoring system status. As illustrated, the patient module 14 can independently or in cooperation with the controller 12 implement one or both of the monitoring pipeline 200 and the disconnect detection algorithm 400.

The one or more electrodes 22 can include one or more recording electrodes configured to detect electrical potentials. The electrodes 22 can be disposed on an electrode body material that facilitates connection of the electrode 22 to a desired portion of the patient's body. For example, the electrode body can be generally planar and include an adhesive surface configured for holding the one or more electrodes 22 to a desired location on the patient. The one or more electrodes 22 can include a cable configured to electrically connect the electrodes 22 to another portion of the system 10, such as the patient module 14.

The display 34 can be a device configured to graphically communicating information to the user. In some examples, the display 34 can include a touch screen for receiving input from a user. In some examples, the display 34 is part of a surgical cart. In other examples, the display 34 can be a head mounted display, an augmented reality display, or a virtual reality display.

For the sake of brevity, additional details of the neurophysiology system 10 are not discussed herein. The neurophysiology system 10 can include one or more aspects of the neurophysiologic monitoring system described in U.S. Pat. No. 9,392,953, filed Sep. 19, 2011, which is hereby incorporated herein by reference in its entirety for any and all purposes. Further, this neurophysiology system 10 is just one example of the systems that can benefit from techniques described herein. In addition, although certain components are shown as separate or in particular locations, they need not be. For example, the monitoring pipeline 200 and the disconnect detection algorithm 400 can be implemented in the patient module 14 or across various components of the system 10, such as both the controller and the patient module 14. Further, the controller 12 can be implemented in the patient module and need not necessarily be contained in separate housings. The system 10 can implement a neuromonitoring pipeline, examples of which are shown in FIGS. 2 and 3.

Figure 2:
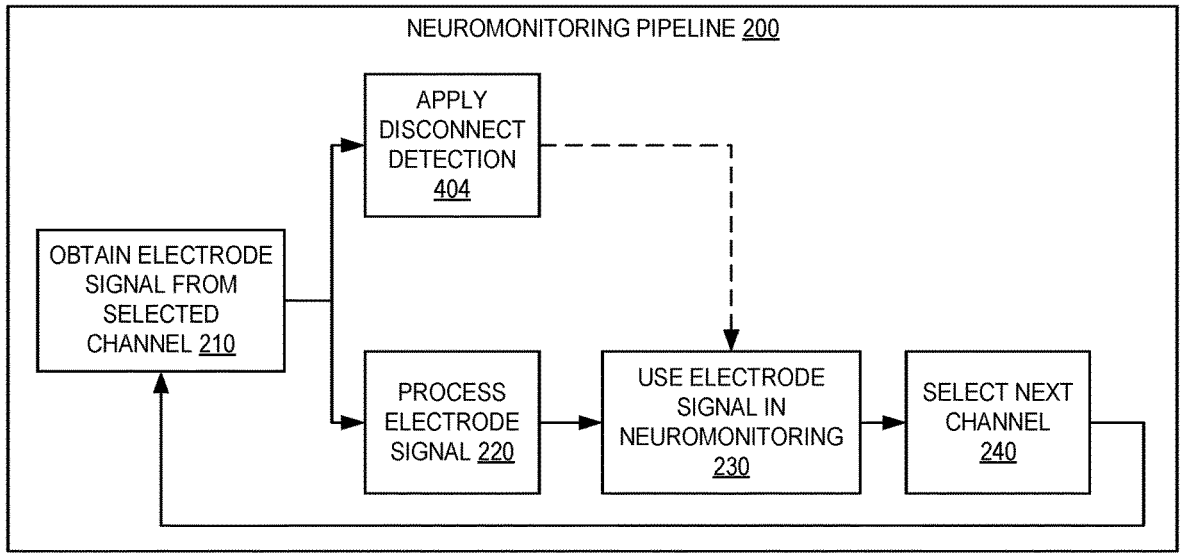
FIG. 2 illustrates a first example implementation of a neuromonitoring pipeline.
Figure 3:
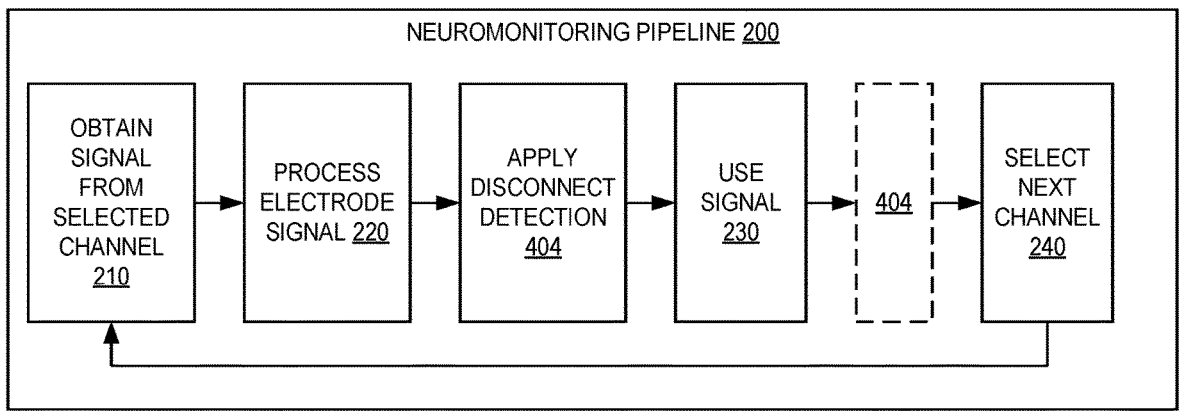
FIG. 3 illustrates a second example implementation of the neuromonitoring pipeline.

FIG. 2 illustrates a first example implementation of the neuromonitoring pipeline 200. The described components of the neuromonitoring pipeline 200 can be implemented in hardware (e.g., using special purpose microcontrollers or field programmable gate arrays configured to implement operations), software (e.g., processor-executable instructions configured to implement operations), or combinations thereof as part of the system 10. The pipeline 200 can begin with operation 210.

Operation 210 can include obtaining an electrode signal from a selected channel. As discussed above, the patient module 14 can include a plurality of recording channels. The operation 210 can include selecting one or more of such channels to record from, such as based on a predetermined order (e.g., in numerical order), based on a schedule (e.g., certain channels are scheduled to be monitored more or less frequently than others), based on user selection, based on a list of active channels (e.g., only those channels that are in use, such as by having an electrode connected thereto as automatically or manually determined), based on other techniques, or combinations thereof. The obtaining or recording of the electrode signal may include recording a signal from the channel to memory for a predetermined amount of time or may include processing the signal obtained from the channel in real time. Signals, as discussed herein, can take any of a variety of forms. In an example, the signal is an actual waveform of recorded energy over a predetermined amount of time. The signal can be raw data recorded or a set of one or more representative characteristics of the raw data usable with the techniques described herein to achieve desired results (e.g., sufficiently accurate electrode disconnect detection). Following operation 210, the flow can move to both a disconnect detection stage 404 and operation 220.

Figure 4:
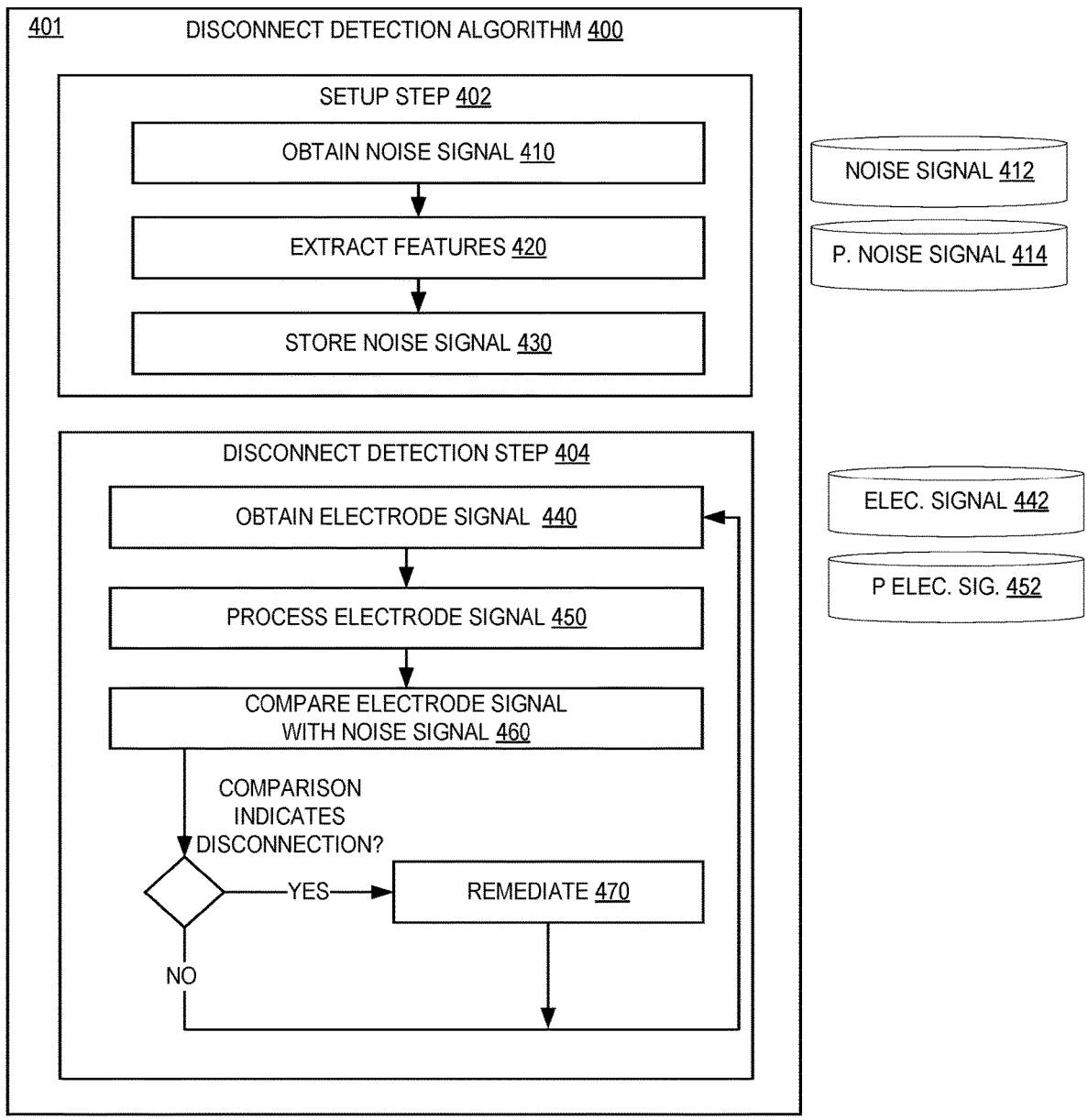
FIG. 4 illustrates a first example method for implementing a disconnect detection algorithm.

The disconnect detection stage 404 can include applying disconnect detection, which is described in more detail in relation to FIG. 4. In an example, the pipeline 200 can include providing the electrode signal obtained in operation 210 to a running or to-be-run disconnect detection process. As further illustrated, an output of the disconnect detection operation 404 can feed into or otherwise affect the use of the electrode signal in neuromonitoring 230, such as preventing the signal from being used in neuromonitoring or by setting a flag indicating that the signal may be from a disconnected electrode.

Operation 220 includes processing the electrode signal obtained in operation 210. For example, the processing can include various hardware or software pre-processing steps to prepare the electrode signal for use in neuromonitoring in operation 230. For example, the operation 220 can include applying a noise reduction filter. Example processing can include applying one or more filters, such as a comb filter, a high-pass filter, a low-pass filter, a notch filter, other filters, or combinations thereof. The flow of the pipeline can move to operation 230.

Operation 230 can include using the processed electrode signal in neuromonitoring. Such a process can include using the processed electrode signal in one or more of basic stimulated EMG, dynamic stimulated EMG, XLIF neuromonitoring, twitch testing, MEP manual neuromonitoring, and MEP Automatic neuromonitoring, SSEP, free-run EMG, other neuromonitoring, or combinations thereof. Example neuromonitoring techniques include those described in U.S. Pat. No. 8,206,312 (filed 2005 Sep. 22); U.S. Pat. No. 9,066,701 (filed 2012 Feb. 6); and US 2012/0095360 (filed 2008 Oct. 15), which are all hereby incorporated herein by reference for any and all purposes. The flow of the pipeline 200 can move to operation 240.

Operation 240 includes selecting a next channel. In some examples, the system 10 can include a series of numbered channels and the selection of the next channel can include selecting a next channel in numerical order. Where the highest numbered channel is the current channel, selecting the next channel can include returning to a first channel with or without a delay of a predetermined length. Following operation 240 the flow of the pipeline can return to operation 210.

In another example, the operations are as described in FIG. 2, but the processed electrode signal in operation 220 is provided to both the disconnect detection operation 404 and neuromonitoring 230 (e.g., the apply disconnect detection operation 404 follows the processing electrode signal operation 220, rather than directly from the obtaining electrode signal operation 210). The prior application of the processing (e.g., removal of noise) can affect how the disconnect detection is applied.

FIG. 3 illustrates a second example neuromonitoring pipeline 200. Here, the operations are as described in FIG. 2, but the application of the disconnect detection 220 occurs in series before or after the use of the signal in neuromonitoring.

FIG. 4 illustrates an example method 401 for implementing the disconnect detection algorithm 400. The described components of the algorithm 400 can be implemented in hardware (e.g., using special purpose microcontrollers or field programmable gate arrays configured to implement operations), software (e.g., processor-executable instructions configured to implement operations), or combinations thereof. As illustrated, the method 401 can be broken into two primary stages: a setup stage 402 and a disconnect detection stage 404. The setup stage 402 can be a portion of the disconnect detection algorithm that generates data for later use. The setup stage 402 may be performed at various times. In an example, the setup stage 402 is performed as part of an initial setup of the controller 12 or the patient module 14 (e.g., during manufacturing or during initial installation with a purchaser). In some examples, the setup stage 402 is performed during an operation setup portion (e.g., during the configuration of the system 10 for performing surgery on the patient). The disconnect detection stage 404 can be a portion of the algorithm 400 that is performed during surgery to detect and alert the user that an electrode may have become disconnected from the patient. The method 401 can begin with operation 410 of the setup stage 402.

Operation 410 includes obtaining a noise signal 412. For example, the operation 410 can include recording a signal from a channel while an electrode connected to the channel is in an open loop. In an example, the noise signal 412 can be obtained from a source other than the one or more electrodes. In an example, the noise signal 412 can be recorded from a channel (e.g., port) before an electrode is connected to the channel. In a further example, the noise signal 412 can be a saved noise signal that is stored in the memory 38. Such a saved noise signal 412 can be created during a manufacturing process or from a prior configuration. In some examples, the noise signal 412 is a selected based on determining a kind of noise signal expected to be detected (e.g., based on the geography in which the machine is operating). Following operation 410, the flow of the method 401 can move to operation 420.

Operation 420 can include extracting features from or otherwise processing the noise signal 412 to form extracted features or a processed noise signal 414. For example, the processing can include calculating power spectral density of the noise signal 412. For example, the power spectral density inclusion can include calculating a non-negative function of frequency that is Fourier transform of an autocorrelation sequence. The processing can include determining an average power in the signal over frequency band. The autocorrelation sequence can be a sequence that measures the degree of similarity between samples of a real-valued signal at a lag is defined.

In an example, the autocorrelation sequence is calculated as:

$$r_x(l) = \sum_{n=-\infty}^{\infty} x(n)x(n-l)$$

where x(n) corresponds to samples of a real valued signal at a lag l. In an example, the power spectral density is calculated as a Fourier transform of the autocorrelation sequence:

$$S_{xx}(\omega) = \sum_{l=-\infty}^{\infty} r_x(l)e^{-j\omega l}$$

The resulting power spectral density calculation performed on the noise signal 412 to form the processed noise signal 414. In some examples one or more additional operations are performed on the noise signal 412.

In some examples the noise signal 412 was previously processed and need not be processed again. For instance, the noise signal 410 may have been processed (e.g., have its features extracted) via the device or process that obtained the noise signal 412 includes a processing operation. In such instances the system 10 may mark the stored noise signal as being processed and this operation 420 is skipped.

Following operation 420, the flow of the method 401 can move to operation 430.

Operation 430 can include storing one or both of the noise signal 412 or the processed noise signal 414. For example, the operation 430 can include storing the noise signal 412 or the processed noise signal 414 to the memory 38.

The disconnect detection stage 404 can be performed as part of neuromonitoring pipeline 200, such as is described above in relation to FIGS. 2 and 3.

Operation 440 can include obtaining an electrode signal 442. For instance, the electrode signal 442 can be an electrode signal 442 recorded for a predetermined amount of time on a selected channel of a plurality of channels (e.g., each channel can correspond to electrode channels of the patient module 14). The electrode signal 442 can be received from another portion of the system 10, such as by being pushed or pulled from another process (e.g., corresponding to operation 310 or 320 of the pipeline 200). Following operation 440, the flow of the method 401 can move to operation 450.

Operation 450 can include processing the electrode signal 442 to form a processed electrode signal 452. Such processing can be in addition to prior processing, if any, performed on the originally-obtained signal that eventually became electrode signal 442. In an example, the operation 450 can include applying the same processing applied in operation 420. In an example, substantially the same processing applied in 420 can be applied, such that the resulting processed electrode signal 452 and the processed noise signal 414 can be usefully compared in order to achieve results described herein. Following operation 450, the flow of the method 401 can move to operation 460.

Operation 460 can include comparing one or both of the electrode signal 442, 452 with one or both of the noise signals 412, 414. For example, the comparison can include comparing the processed electrode signal 452 with the processed noise signal 414. The comparison can be such that the result is useful in determining whether the electrode signal 442, 452 is consistent with a signal indicating that the electrode is disconnected from the patient. In an example, the comparison is based on the results of a linear correlation between the signals, such as by determining a Pearson correlation coefficient. Other comparisons that can be used include cosine similarity, Euclidean distance, Mahalanobis distance, mutual information, Spearman's correlation, other comparisons, or combinations thereof. If the correlation is sufficiently high (e.g., the correlation satisfies a predetermined threshold), then it can be determined that the electrode signal is likely to be obtained from an electrode that was disconnected from a patient. In another example, the comparison is based on a statistical analysis of the signals.

In an alternative implementation, in addition to or instead of comparing the electrode signal 442, 452 with the noise signal 412, 414, the electrode signal 442, 452 is compared with a known good signal where an electrode is connected. The electrode signal 442, 452 can then be compared to both the sample noise signal 412, 414 and the sample electrode signal 442, 452, and is classified (e.g., as connected or disconnected) based on which the electrode signal 442, 452 is more similar too. In another implementation, rather than obtaining and storing a noise signal 412, 414, a known signal from a connected electrode is obtained (e.g., as part of the patient preparation process or as part of a preoperative process). The incoming electrode signal 442, 452 is then compared to the stored electrode signal and classified as connected or disconnected based on the comparison (e.g., responsive to being sufficiently similar, the electrode is classified as connected).

In some examples, the comparison or thresholds can vary depending on an amount of pre-processing performed on the signals. For example, in some instances (see example FIG. 3), the signal is pre-processed to remove or reduce noise, then the threshold or other comparison measures can be modified to account for the reduction of noise.

Following operation 460, responsive to the comparison indicating disconnection of an electrode (e.g., the comparison resulting in a value that satisfies a threshold), the flow of the method 401 can move to operation 470, otherwise the flow of the method 401 can return to operation 440.

Operation 470 includes performing remediation. For example, the remediation can be causing the controller 12 or the patient module 14 to alert a user to the potential electrode disconnect issue. The alert can be in any of a variety of forms (e.g., audible, visual, haptic, other forms, or combinations thereof). The remediation can include sending a message to a remote neuromonitoring device indicating the potential change in the electrode status. In an example, remediation can include causing a light on an electrode 22 or patient module 14 to illuminate (e.g., flash) to indicate that an electrode is disconnected or even which electrode is disconnected. In an example, the remediation can include throwing an error or setting a flag in the system 10 to indicate a potential fault. In an example, the flag can indicate potential unreliability of the signal being received from the selected channel. As a result, the signals received from the selected channel can be disregarded for neuromonitoring purposes. In an example, the indication can include changing a user interface element of the signal to indicate that the signal is unreliable. In some examples, the remediation includes indicating signals received from the electrode corresponding to the electrode signal 440 are not valid. For example, this can include causing the system 10 to disregard the electrode signal for the purposes or neuromonitoring or indicating that the system should not rely on signals from that electrode until the system 10 receives an indication otherwise (e.g., detecting that signals corresponding to that electrode no longer correlate to noise or receiving input from a user indicating that the electrode has been reconnected). Example alerts and other user interface elements are shown in relation to FIG. 5. Following operation 470, the flow of the method 401 can return to operation 440.

In a further example of remediation, the disconnect detection can be used to identify when the electrode lost or gained contact with the patient, such as by checking where the incoming signal switched from being classified as "signal" to "noise" (or vice versa). This classification can assist users or systems in identifying when in the surgery the disconnection happened. This classification can facilitate analysis to a recorded neural monitoring session to mark out regions where the electrode's signal was lost. This might be useful in post-procedure analysis of nerve health or of overall reliability of the electrodes. Such information can be useful in determining a stage of the procedure (e.g. changing patient's position) where the electrode tends to fall off so as to improve reliability of neural monitoring in the future.

In an example, a similar method 401 can be applied to determine that electrodes are newly properly connected. For example, where a signal from an electrode channel once indicated that the electrode was disconnected and then a new signal is received indicating that the electrode is properly connected, then the system 10 can use such an indication. For example, the system 10 can automatically cease one or more remediation measures (e.g., alerts, disregarding signals corresponding to the channel, etc.).

While the example of FIG. 4 shows separate setup and disconnect detection steps, they need not be separate or need not be performed separately in series. As an example, instead of having a constant stored noise signal 412 throughout the procedure, the stored noise signal 412 can be updated periodically. While ideally the stored and incoming noise signals should be the same or highly correlated, there may nonetheless be some slight change in the environmental conditions that affect the noise. To account for such environmental changes, the stored noise signal 412 can be updated during the procedure from disconnected electrodes. Such updating can take any of a variety of forms, such as a weighted average of the previously stored noise and current noise (e.g., recorded signal from current epoch when electrode is disconnected from the recording site).

Figure 5:
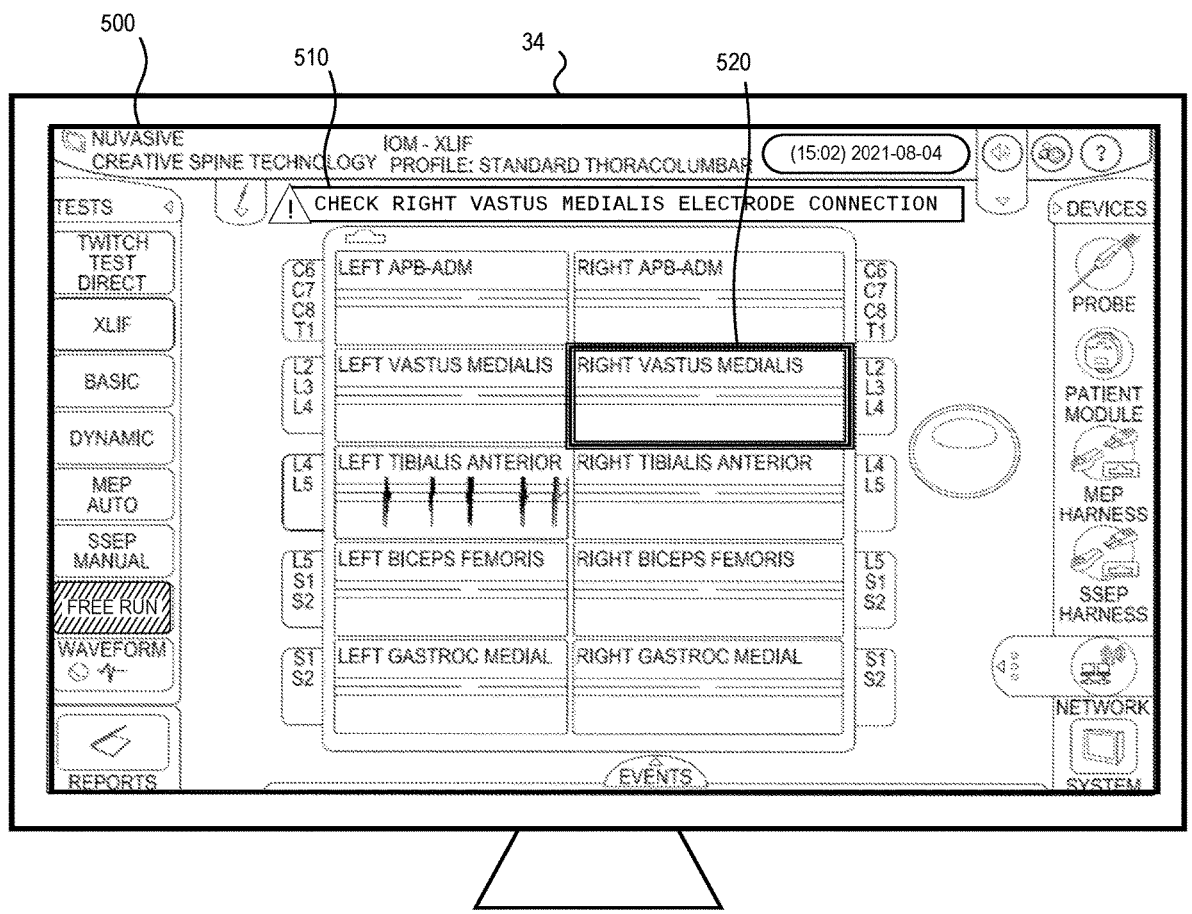
FIG. 5 illustrates an example user interface provided by a controller at a display.

FIG. 5 illustrates an example user interface 500 provided by the controller 12 at the main display 34. The user interface 500 displays information about the system 10 operating in a free-run EMG monitoring mode that continuously listens for spontaneous muscle activity that may be indicative of potential danger to a nerve. As illustrated, the user interface 500 illustrates an alert 510 displayed that visually indicates a potential problem with one of the electrode connections. In examples, an identifier of the channel or electrode (e.g., an identifier of a channel having the issue or a name corresponding to its anatomical location as determined by a lookup table or specified by the user) is provided. As illustrated, the alert 510 asks the user to "check right vastus medialis electrode connection" for a potential problem. This example customizes the alert 510 to indicate that the problem is with an electrode connection at the patient's right vastus medialis.

The user interface 500 further includes a highlight 520 that is one or more user interface elements configured to draw the user's attention to a particular portion of the user interface 500. In this figure, the highlight 520 is configured to draw the user's attention to the electrode channel (here corresponding to the right vastus medialis) that is potentially disconnected.

Figure 6:
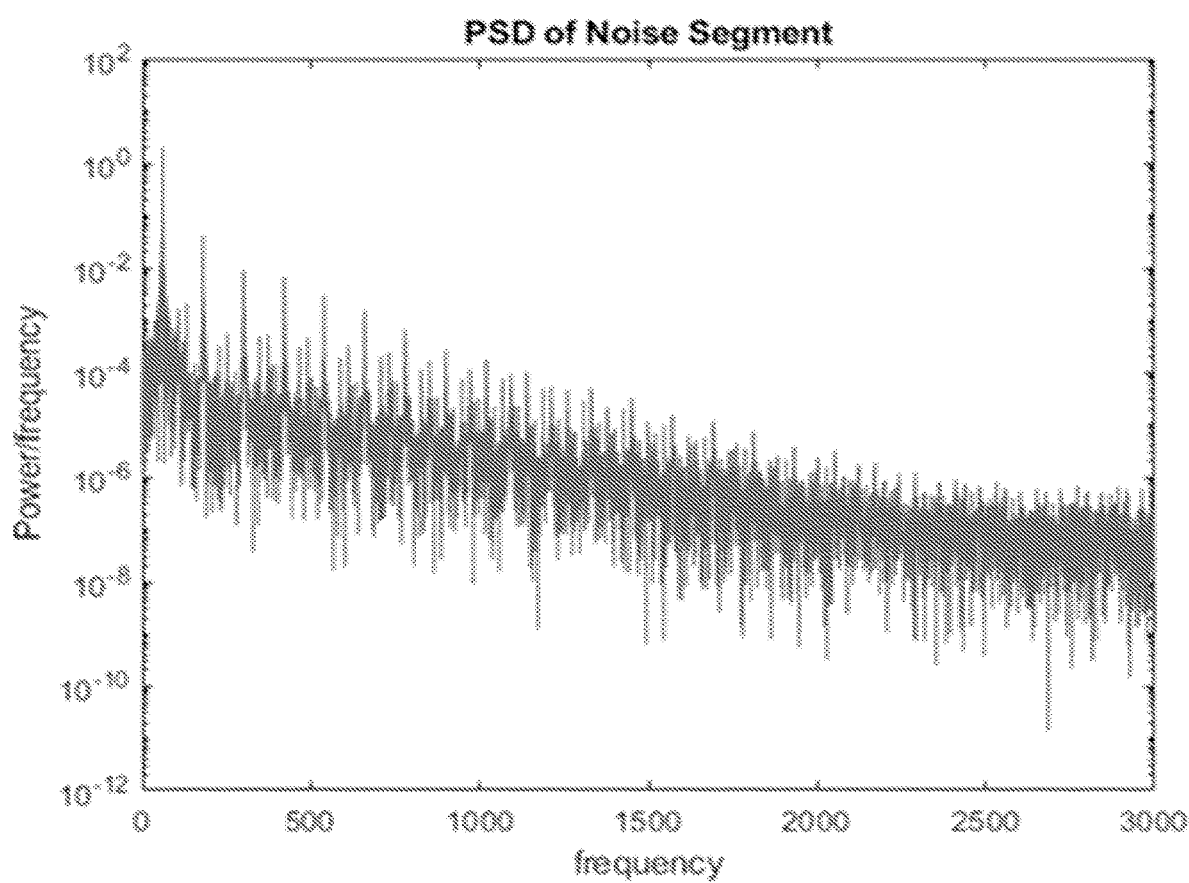
FIG. 6 illustrates an example chart showing a power spectral density of a noise segment corresponding to an electrode removed from a patient's skin.
Figure 7:
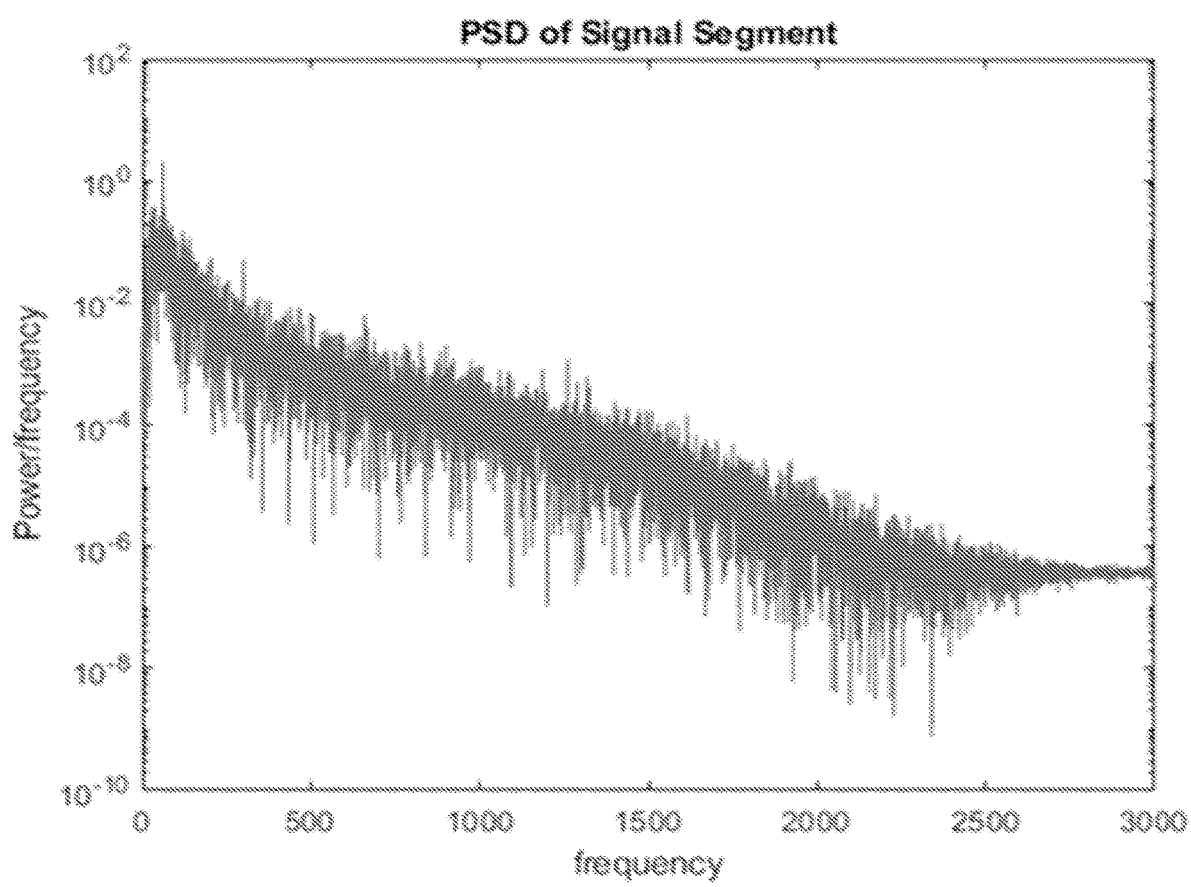
FIG. 7 illustrates an example chart showing a power spectral density of a signal segment corresponding to a signal corresponding to an electrode properly coupled to the patient's skin.
Figure 8:
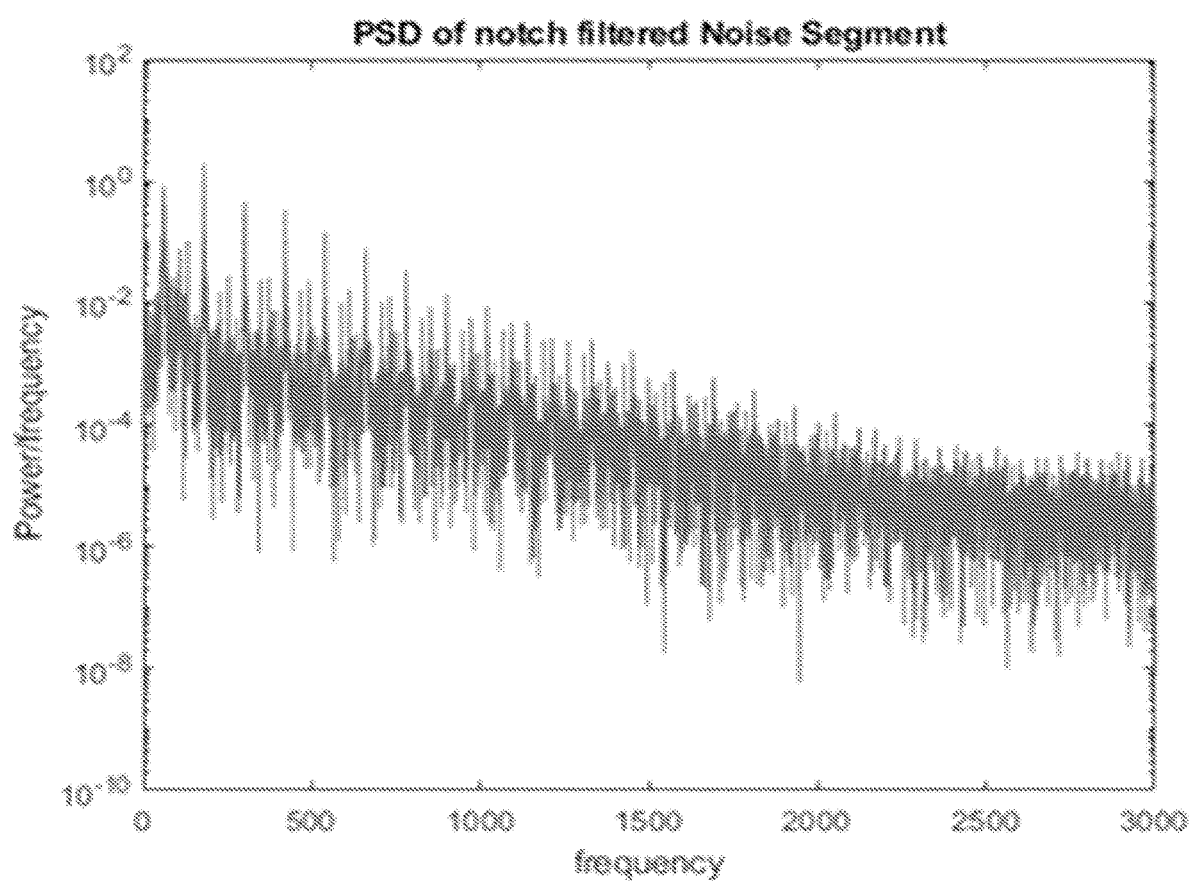
FIG. 8 illustrates an example chart showing a power spectral density of a notch filtered noise segment corresponding to an electrode removed from a patient's skin.
Figure 9:
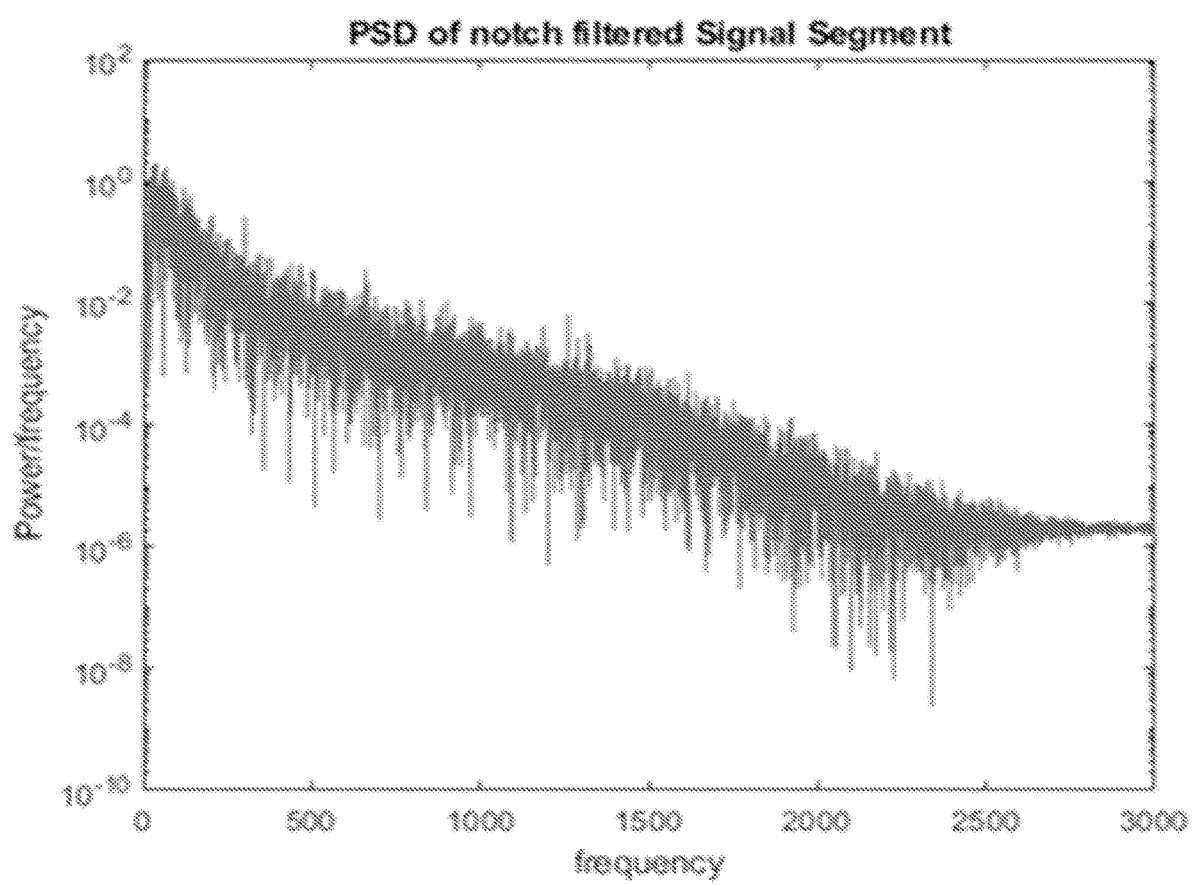
FIG. 9 illustrates an example chart showing a power spectral density of a notch filtered signal segment corresponding to a signal corresponding to an electrode properly coupled to the patient's skin.

FIGS. 6-9 illustrate example charts showing power spectral density of noise or signal segments. FIG. 6 illustrates an example chart showing a power spectral density of a noise segment corresponding to an electrode removed from a patient's skin. FIG. 7 illustrates an example chart showing a power spectral density of a signal segment corresponding to a signal corresponding to an electrode properly coupled to the patient's skin. FIG. 8 illustrates an example chart showing a power spectral density of a notch filtered noise segment corresponding to an electrode removed from a patient's skin. FIG. 9 illustrates an example chart showing a power spectral density of a notch filtered signal segment corresponding to a signal corresponding to an electrode properly coupled to the patient's skin.

Figure 10:
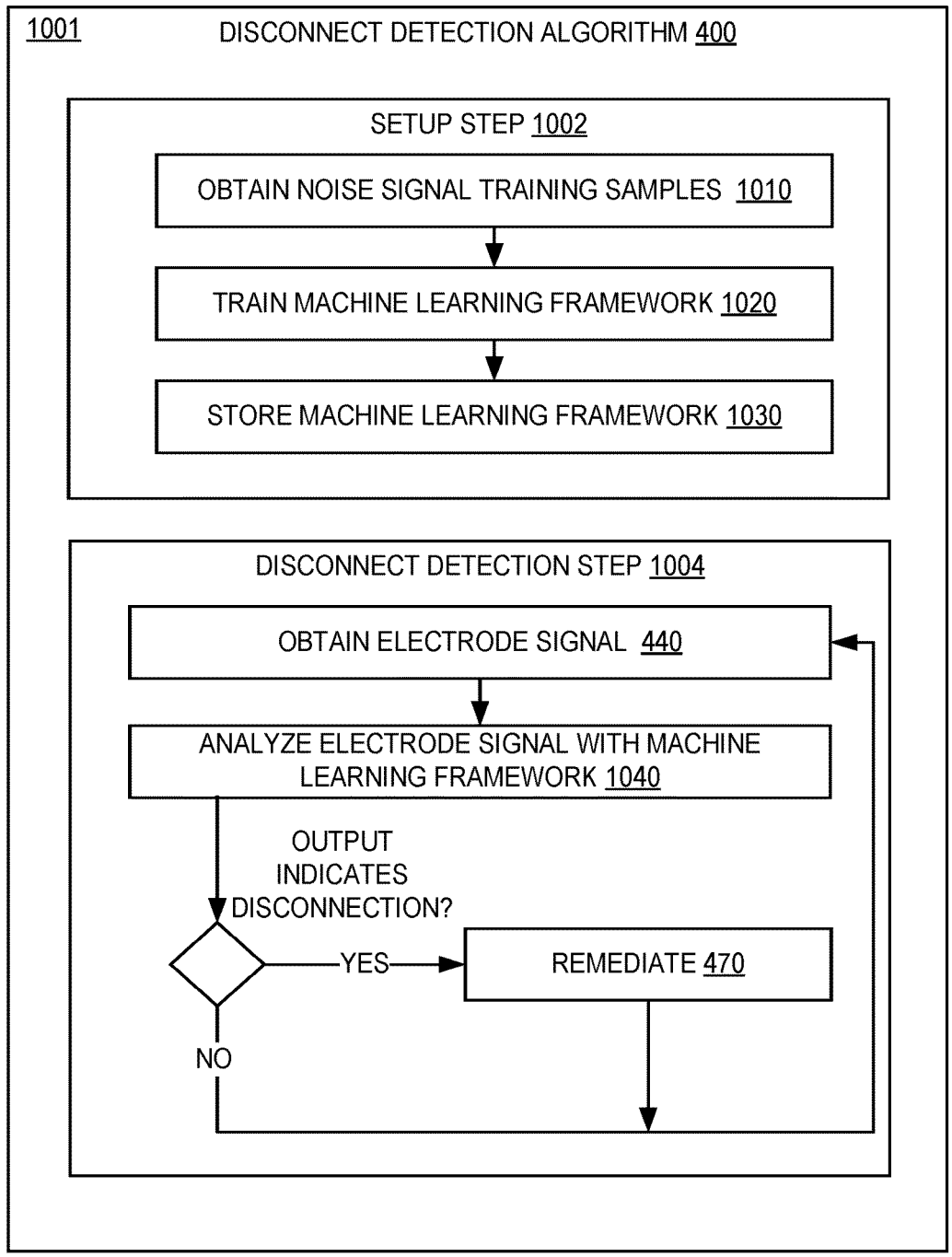
FIG. 10 illustrates a second example method for implementing the disconnect detection algorithm.

FIG. 10 illustrates a second example method 1001 for implementing the disconnect detection algorithm 400. As illustrated, the method 1001 can be broken into two primary stages: a setup stage 1002 and a disconnect detection stage 1004. The setup stage 1002 can include one or more characteristics of the setup step 402 discussed above. The disconnect detection stage 1004 can include one or more characteristics of the disconnect detection stage 404 discussed above. The method 1001 can begin with operation 1010 in the setup stage 1002.

Operation 1010 includes obtaining noise signal training samples. The noise signal training samples are examples of noise signals suitable for training a machine learning framework. Such noise signals can be real-world or synthetic examples of a signal from a channel while an electrode connected to the channel is in an open loop. The noise signal training samples need not only include positive training samples but also negative training samples (e.g., samples of signals from electrodes that are properly attached). The training samples can further include labels for the samples (e.g., expected output given the sample as input). Following operation 410, the flow of the method 401 can move to operation 420.

Operation 1020 can include training a machine learning framework using the noise signal training samples. One or more aspects of the machine learning framework can be implemented with or based on TENSORFLOW by GOOGLE INC., PYTORCH by the PYTORCH community, and or other open or closed source machine learning libraries. The machine learning framework can include one or more machine learning models that are structures for learning. The models can include one or more structures representing machine learning nodes (e.g., nodes of a neural network, decision tree, or other kind of neural network), connections between nodes, weights, matrices, other structures, or combinations thereof. The machine learning framework can define procedures for establishing, maintaining, training, and using the one or more machine learning models. Training the machine learning framework can include providing the noise signal training samples as input to the machine learning framework in a useful format (e.g., after converting the noise signal training samples to the useful format), processing the samples with the machine learning framework, and receiving an output from the machine learning framework. The output can be compared with an expected result defined in association with the training samples as part and a loss determined using a loss function (e.g., mean squared error). The machine learning framework (e.g., one or more models thereof) can be modified based on the output (e.g., based on a difference between the output and the expected result). The process of training and modifying can be repeated until the error is sufficiently small. Following operation 1020, the flow of the method 1001 can move to operation 1030.

Operation 1030 can include storing the trained machine learning framework. For example, the operation 1030 can include storing the machine learning framework in the memory 38.

The disconnect detection stage 1004 can be performed as part of neuromonitoring pipeline 200, such as is described above in relation to FIGS. 2 and 3.

Operation 440 can include obtaining an electrode signal 442, which can be as discussed above. Following operation 440, the flow of the method 1001 can move to operation 1040.

Operation 1040 includes analyzing the electrode signal 442 with the machine learning framework. The operation can include providing the electrode signal 442 as input to the machine learning framework, processing the electrode signal 442 with the machine learning framework, and obtaining an output of the machine learning framework. The processing can vary depending on the configuration of the machine learning framework.

Following operation 1040, responsive to the output of the machine learning framework indicating disconnection of an electrode (e.g., the output satisfying a threshold), the flow of the method 1001 can move to operation 470, otherwise the flow of the method 401 can return to operation 440.

Operation 470 includes performing remediation, such as is discussed above. Following operation 470, the flow of the method 1001 can return to operation 440.

While examples herein are discussed primarily in the context of surgical neuromonitoring, techniques described herein can be applied in other contexts and with other sensors. Examples include neurophysiological recording in research (e.g. neuroscience research), EEG (electroencephalograms), or MEG (magnetoencephalography), recording brain electrical activity, sensors for health monitoring (e.g. smart watches), electrical stimulation for physical therapy, other contexts, or combinations thereof. Beyond human-electrode contact, the techniques describe herein can be applied to other electrical applications where a wire or connector may lose contact (e.g. in electrical components outdoors where weather might cause a disconnect).

Any of the features or attributes of the above described embodiments and variations can be used in combination with any of the other features and attributes of the above described embodiments and variations as desired. Various modifications, additions and other alternative embodiments are possible without departing from the true scope and spirit. The embodiments presented herein were chosen and described to provide an illustration of various principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

The invention claimed is:

1. A method for detecting whether an electrode is connected, comprising:
storing a noise signal, the noise signal being a recording of a channel taken before an electrode is connected to the channel;
during a surgical procedure, obtaining an electrode signal from the channel;
performing a comparison on the electrode signal and the noise signal to generate an amount of linear correlation of the noise signal and the electrode signal;
determining if the amount of linear correlation satisfies a predetermined threshold; and
responsive to determining the amount of linear correlation satisfies the predetermined threshold, determining the electrode signal is disconnected from a patient and providing an alert that the electrode is disconnected from the patient.

2. The method of claim 1, wherein performing the comparison further includes comparing a power spectral density of the electrode signal with a power spectral density of the noise signal.

3. The method of claim 1, further comprising determining a Pearson correlation coefficient.

4. The method of claim 1, wherein performing the comparison includes determining a cosine similarity, Euclidean distance, Mahalanobis distance, mutual information, or Spearman's correlation.

5. The method of claim 1, further comprising:
processing the noise signal, thereby resulting in a processed noise signal; and
storing the processed noise signal.

6. The method of claim 5, wherein processing the noise signal includes extracting features from the noise signal.

7. The method of claim 1, further comprising training a machine learning framework using the noise signal as input, thereby resulting in a trained machine learning framework.

8. The method of claim 7, storing the trained machine learning framework.

9. A method for detecting whether an electrode is connected, comprising:
obtaining noise signal training samples, the noise signal training samples being a recording of a channel taken before an electrode is connected to the channel;
training a machine learning framework using the noise signal training samples;
storing the trained machine learning framework in memory;
obtaining an electrode signal;
providing the electrode signal as input to the machine learning framework;
processing the electrode signal with the machine learning framework;
obtaining an output of the machine learning framework; and
determining the output of the machine learning framework indicates disconnection of the electrode and providing an alert that the electrode is disconnected from a patient.

10. The method of claim 9, wherein processing the electrode signal with the machine learning framework includes performing a comparison on the electrode signal and the noise signal to generate an amount of linear correlation of the noise signal and the electrode signal.

11. The method of claim 9, wherein the machine learning framework includes one or more machine learning models that are structures for learning.

12. The method of claim 11, wherein the machine learning framework can define procedures for establishing, maintaining, training, and using the one or more machine learning models.

13. The method of claim 9, wherein training the machine learning framework includes providing the noise signal training samples as input to the machine learning framework in a useful format.

14. The method of claim 9, further comprising comparing the output with an expected result defined in association with the noise signal training samples and a loss determined using a loss function.

15. The method of claim 14, wherein the loss function is mean squared error.

16. The method of claim 14, wherein performing the comparison includes determining a cosine similarity, Euclidean distance, Mahalanobis distance, mutual information, or Spearman's correlation.

17. The method of claim 14, further comprising modifying the machine learning framework based on a difference between the output and the expected result.

18. The method of claim 17, further comprising repeating a process of training and modifying until an error is sufficiently small.

19. A system for detecting whether an electrode is connected, comprising:
- one or more electrodes;
- one or more processors; and
- memory storing instructions that, when executed by the one or more processors, cause the system to perform:
  - storing a noise signal, the noise signal being a recording of a channel taken before the one or more electrodes are connected to the channel;
  - during a surgical procedure, obtaining an electrode signal from the channel;
  - performing a comparison on the electrode signal and the noise signal to generate an amount of linear correlation of the noise signal and the electrode signal;
  - determining if the amount of linear correlation satisfies a predetermined threshold; and
- responsive to determining the amount of linear correlation satisfies the predetermined threshold, determining the electrode signal is disconnected from a patient and providing an alert that an electrode is disconnected from the patient.

20. The system of claim 19, wherein the instructions further cause the system to perform training a machine learning framework using the noise signal as input.

\* \* \* \* \*